United States Patent [19]

Kremer, Jr. et al.

[11] Patent Number: 4,792,097

[45] Date of Patent: Dec. 20, 1988

[54] NON-SPUTTERING NEBULIZER

[75] Inventors: Carl P. Kremer, Jr.; Ann S. Kremer, both of Darien, Conn.; Henry Tom, La Honda, Calif.

[73] Assignee: Mallinckrodt, Inc., St. Louis, Mo.

[21] Appl. No.: 32,381

[22] Filed: Mar. 31, 1987

[51] Int. Cl.[4] ........................ A61M 11/00; B05B 7/30

[52] U.S. Cl. .................................... 239/338; 239/370; 239/432; 128/200.18; 128/200.21; 261/78.1

[58] Field of Search ........................ 239/338, 370, 432; 261/DIG. 65, 78.1; 128/200.18, 200.21; 251/118; 222/547, 564

[56] References Cited

U.S. PATENT DOCUMENTS

| | | | |
|---|---|---|---|
| 3,658,059 | 4/1972 | Steil | 128/200.21 |
| 4,116,387 | 9/1978 | Kremer, Jr. et al. | 239/338 |
| 4,244,556 | 1/1981 | Miller | 251/118 |
| 4,251,033 | 2/1981 | Rich et al. | 239/338 |
| 4,456,179 | 6/1984 | Kremer | 239/338 |
| 4,588,129 | 5/1986 | Shanks | 239/370 |
| 4,657,007 | 4/1987 | Carlin et al. | 128/200.18 |
| 4,669,276 | 6/1987 | Sakai et al. | 239/124 |

FOREIGN PATENT DOCUMENTS

| | | | |
|---|---|---|---|
| 320234 | 3/1957 | Switzerland | 239/338 |

*Primary Examiner*—Andres Kashnikow
*Assistant Examiner*—Karen B. Merritt
*Attorney, Agent, or Firm*—Bernard, Rothwell & Brown

[57] ABSTRACT

An improved nebulizer for substantially complete discharge of liquid before "sputtering" occurs includes a housing having a mist outlet, and an aspirating structure including a nozzle having a base portion at one end thereof within the housing. The nozzle includes a nozzle outlet for discharge of gas under pressure within the housing at end of the nozzle opposite the base portion. The nebulizer further includes an inverted frusto-conical bottom wall disposed about the base portion of the nozzle away from the nozzle outlet, the bottom wall forming a liquid reservoir that drains towards the base portion of the nozzle. The aspirating structure also includes at least one passageway peripherally located with respect to the nozzle, the passageway communicating with the reservoir for aspiration of liquid from the reservoir in response to gas discharged from the nozzle to form a mist. A well that is in communication with the passageway is interposed between the bottom wall and the aspirating structure for collecting and concentrating liquid between the bottom wall and the aspirating structure to avoid "sputtering" of liquid prior to substantially complete discharge of liquid from the nebulizer.

12 Claims, 1 Drawing Sheet

NON-SPUTTERING NEBULIZER

BACKGROUND OF THE INVENTION

1. Field of the Invention

The present invention relates to improvements in nebulizers for producing mists having small particle sizes.

2. Description of the Background Art

Nebulizers and other mist generators have been made for a wide variety of purposes including therapeutic and diagnostic applications in the medical field, as well as non-medical applications. Therapeutic applications include delivery of medication to the lungs and air passageways of a patient. Diagnostic applications include utilization of an aerosolized radioactive isotope for ventilation of the lungs to enable the production of multiple images of relatively high resolution and contrast to facilitate location of emboli, tumors and the like, and to diagnose other diseases affecting the respiratory track.

Diagnosis of respiratory diseases using radioactive aerosols requires mists having exceedingly small particle sizes in order to avoid excessive deposition or rainout of the mist particles in the upper respiratory track of the patient, as well as the oral pharynx, the trachea and at airway intersections. To prevent uneven deposition of the mist between the central and peripheral areas of the lung, radioactive aerosols should be delivered to the lung in a substantially uniform manner, and should have a particle size maintained below about 1.2 microns with the major portion of the particles being well below 1 micron.

Nebulizers that produce exceedingly small particle sizes suitable for diagnosis of respiratory diseases are disclosed in commonly owned U.S. Pat. Nos. 4,116,387 and 4,456,179. The nebulizers disclosed in these two patents both have an inverted frusto-conical bottom wall portion forming a liquid reservoir that slopes downwardly and inwardly towards the base of a pressurized gas nozzle. A passageway extends from the base of the nozzle towards the nozzle outlet to draw liquid from the reservoir in response to gas discharged from the nozzle, and thereby form a mist.

While the nebulizers disclosed in the above-referenced U.S. patents produce aerosols having exceedingly small particle sizes, during use, a phenomenon known as "sputtering" may occur prior to complete discharge of liquid from the reservoir. Once "sputtering" begins, the delivery of nebulized liquid is erratic, reducing the uniformity of the delivery of the radioactive aerosol. Accordingly, there remains a need in the art for a nebulizer that provides substantially complete discharge of liquid from the reservoir before "sputtering" occurs.

SUMMARY OF THE INVENTION

The present invention is applicable to a nebulizer of the type including a housing, and a nozzle within the housing, the nozzle having a base portion at one end thereof and a nozzle outlet for the discharge of gas under pressure at an end of the nozzle opposite the base portion. The nebulizer includes an inverted frustoconical bottom wall disposed about the base portion of the nozzle away from the nozzle outlet. The bottom wall of the nebulizer forms a liquid reservoir that drains towards the base portion of the nozzle. At least one passageway is peripherally located with respect to the nozzle, the passageway communicating with the reservoir for the aspiration of liquid in the reservoir in response to gas discharged from the nozzle to thereby form a mist, which exits the nebulizer through a mist outlet. The invention provides a well interposed between the bottom wall and the nozzle and in communication with the passageway to concentrate liquid to be drawn through the passageway and avoid sputtering of liquid prior to substantially complete discharge of liquid from the nebulizer.

DETAILED DESCRIPTION OF THE PREFERRED EMBODIMENTS

Figure 2:
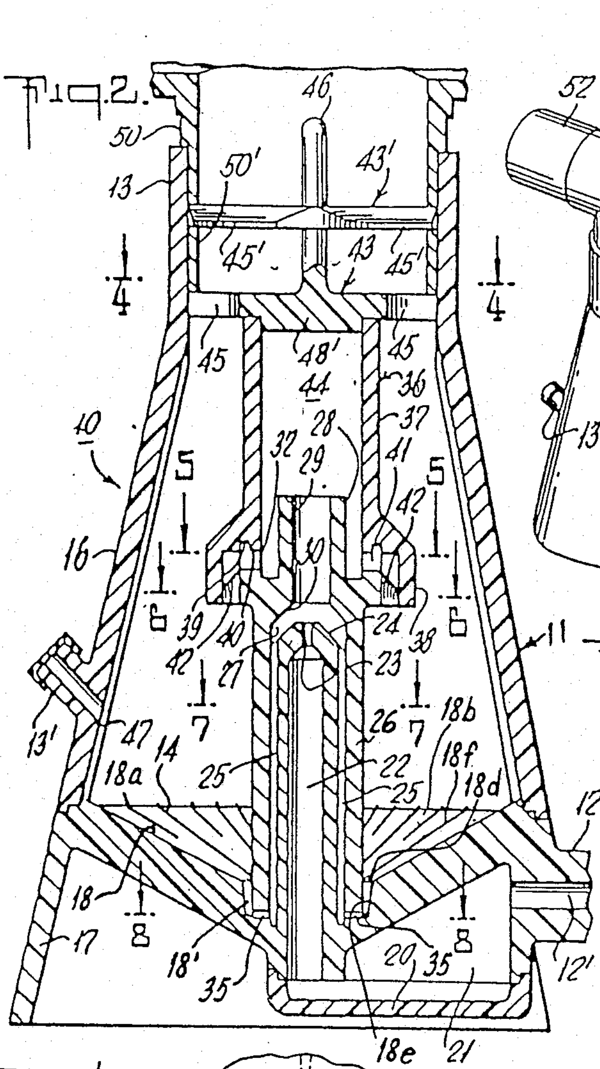
FIG. 2 is an enlarged cross-sectional view of FIG. 1 taken along the line 2—2 thereof, showing a liquid-collecting well according to the invention.
Figure 1:
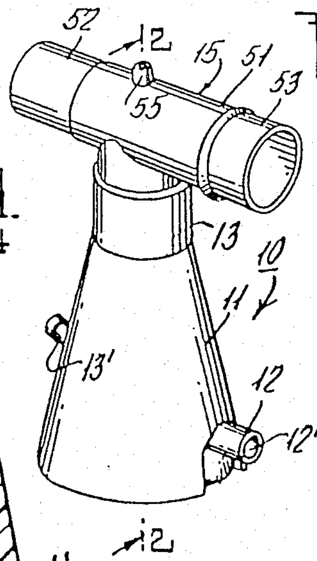
FIG. 1 is a perspective view of one type of nebulizer to which the present invention is applicable.

Referring now to the drawings, and more specifically, to FIGS. 1 and 2, the present invention is applicable to a nebulizer, an example of which is illustrated and generally denoted by the numeral 10 and comprises an outer frusto-conical housing 11, a compressed air inlet 12 and an outlet 13 for the nebulized liquid 14 contained within the housing 11. A T-tube 15 may be affixed to the top of the nebulizer housing 11 as illustrated in FIG. 1. This T-tube is particularly useful when the device is being employed for therapeutic purposes. It will be understood, however, that the nebulizer in accordance with the invention is useful for nebulizing other liquids such as oils, paints, chemical solutions and the like when it is desired to uniformly provide a mist having exceedingly fine particles.

More specifically, the housing 11 consists of a frusto-conical sidewall portion 16 terminating in a cylindrical outlet 13, a base portion 17, and a capped liquid inlet 13' for feeding liquid to the reservoir prior to or during the course of producing the mist. The base portion 17 includes an inverted frusto-conical bottom wall 18 forming a liquid reservoir disposed about a nozzle 19 extending upwardly from the center thereof. At least a portion of the space below the bottom wall 18 is closed by a cap 20 to form a closed chamber 21 to receive compressed air or gas entering through the opening 12' on the inlet 12. The nozzle 19 has a central opening 22 which communicates with the chamber 21 and terminates at its upper end in a small outlet opening 23 spaced away from the bottom wall 18.

In the embodiment shown, the upper end of the nozzle 19 is provided with a 45° bevel as denoted by the numeral 24. The angular configuration of the end of the nozzle has been found particularly useful in producing a fine mist. It is evident, however, that angles differing from 45° may also be utilized.

Figure 3:
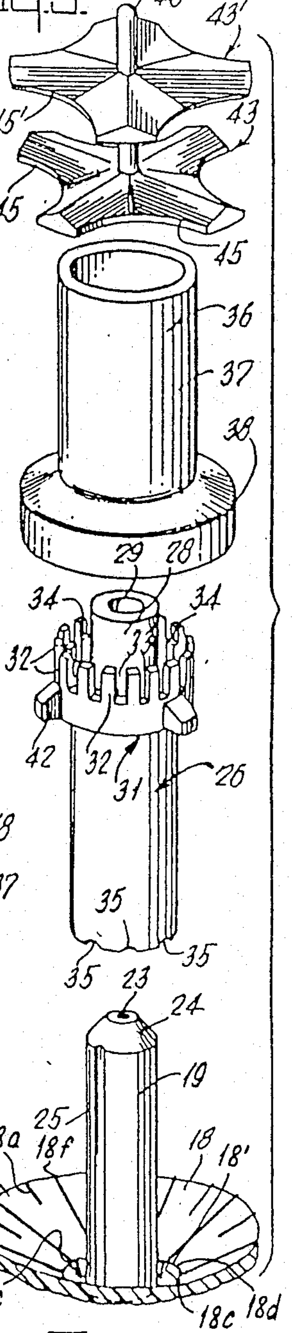
FIG. 3 is an exploded view of the nebulizing structure enclosed within the outer housing as shown in FIG. 2.
Figure 7:
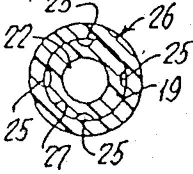
Figure 5:
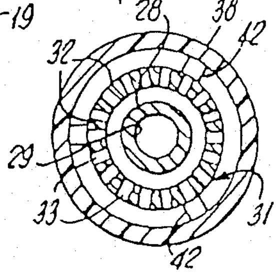
Figure 9:
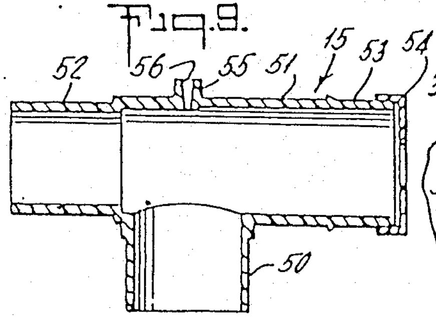
FIG. 9 is a cross-sectional view of the T-tube disposed on top of the nebulizer as illustrated in FIG. 1.
Figure 8:
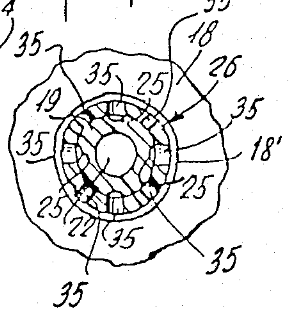

In the illustrated embodiment, the nozzle 19, as viewed in FIGS. 3 and 8, has a plurality of passageways or channels 25 formed in the surface thereof. A sleeve-like cylindrical structure 26 having a central opening 27 slidably receives the nozzle 19 as will be observed more clearly in FIGS. 2, 7 and 8. The assembled nozzle 19 and cylindrical structure 26 forms a central aspirating structure. The cylindrical structure 26 causes the liquid that is to be nebulized to be drawn upwardly through the channels 25. If desired, a single channel can be provided rather than the plurality of channels 25 shown for drawing liquid towards the tip of nozzle 19.

The upper end 28 of the cylindrical structure 26 is of reduced diameter and has an opening 29 which is of reduced diameter and which communicates with the opening 27. The opening 27 terminates above the end of the nozzle 19 in a conical convergent portion 30, preferably at a 45° angle, which communicates with the opening 29. The cylindrical structure further includes an annular portion 31 of enlarged diameter which has a plurality of spaced upwardly extending elements 32 forming intervening slots 33. The upper end of each of the elements 32 is of reduced section to form a shoulder 34 as will be observed more clearly in FIG. 3. The bottom end of the cylindrical structure includes a plurality of slots or grooves 35 to admit fluid to the channels 25, formed in the nozzle 19, during the aspirating process.

A second cylindrical structure 36 is arranged to cooperate with the cylindrical structure 26 as will be observed more clearly in FIGS. 2 and 3. The structure 36 has a cylindrical portion 37 terminating in a lower portion 38 of enlarged diameter and in the nature of a skirt. If desired, the skirt portion 38 can extend downwardly towards bottom wall 18 a considerably longer distance than is shown. The inner surface of the skirt portion 38 as viewed in FIG. 2 has an annular recess 39 to receive the upper ends of the elements 32 with the shoulder 34 of the elements 32 bearing against the surface 40. With this arrangement, the spaced elements cooperate with the cylindrical structure 36 to form a plurality of openings 41. The structure 26 also includes a plurality of outwardly extending spacing or aligning members 42 which engage in the inner surface of the skirt portion 38 as shown in FIG. 2 to insure proper alignment of the two cylindrical structures 26 and 36.

The top of the cylindrical structure 36 is closed by a top cap 43 having an annular portion 48' engaging the top of the cylindrical portion 37 of the structure 36 to form a closed chamber 44. A plurality of recesses 45 are formed in the edge of the top cap to permit the flow of the mist upwardly into the T-tube 15 or be discharged into the atmosphere or other tubing that may be connected thereto. To facilitate removal of the top cap 43, a short rod-like extension 46 is secured thereto which can be readily gripped by the fingers.

With the apparatus thus far described, a liquid to be nebulized is placed in the bottom of the housing 16 surrounding the nozzle 19. Air is fed through the opening 12' into the chamber 21 whereupon it is discharged upwardly through the openings 22 and 23 in the nozzle 19. This aspirates the liquid which is drawn up through the channels 25 in the side of the nozzle 19 and produces a mist which enters a first chamber directly ahead of the nozzle. The mist then passes into a second chamber formed by the opening 29 in the tubular member 28 whereupon it is discharged into chamber 44. The mist then passes downwardly and is exhausted through the openings 41 formed by the spaces 33 between the vertically disposed elements 32 and into the frusto-conical housing surrounding the nebulizing structure. The resultant mist is then discharged upwardly through the recesses or openings 45 in the top cap 43.

The particles generated by this nebulizer while in the submicron particle size nevertheless, do include particles that may range in the order of a half micron or possibly larger. While a substantial portion of these larger particles are removed by reason of the turbulence created in the production of the mist in its direction through the chambers and ports, some of the larger particles, nevertheless, remain and are discharged with the mist. Since the smaller particles being considerably lighter in weight tend to rise on entering the chamber surrounding the nozzle and the structure forming the chamber 44, the heavier particles, however, tend to continue in a given path or follow a larger radially path than the smaller particles. A substantial portion of these larger particles therefore strike the converging housing wall and are returned to the reservoir to be drained to the well. Additional large particles may be removed by the utilization of a plurality of ridges 47 formed on the inner side of the wall 16. These ridges tend to intercept more of the larger particles and either break them up into smaller particles or return the liquid back to the reservoir to be drained towards the well. The ridges are preferably of the order of 0.85 mm to 2 mm in height and may be spaced 1 to 5 mm apart. The height of the ridges will be dependent on the viscosity of the liquid being nebulized.

Figure 2A:
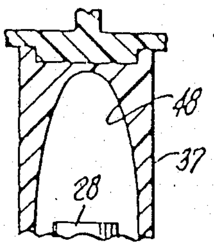
FIG. 2*a* is a fragmentary portion of FIG. 2 showing a modified embodiment of a chamber therein.
Figure 4:
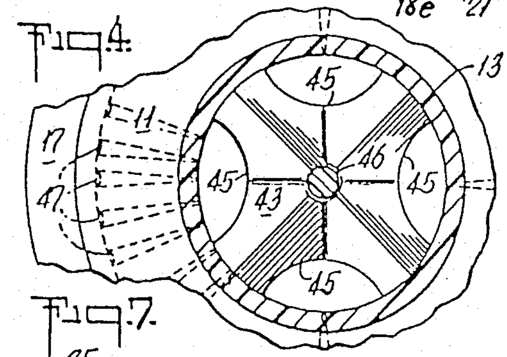
FIGS. 4, 5, 6, 7 and 8 are cross-sectional views of FIG. 2 taken along the lines 4—4, 5—5, 6—6, 7—7, and 8—8 of FIG. 2.
Figure 6:
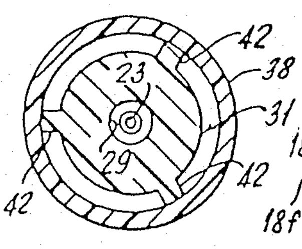

In order to further increase the turbulence of the mist as it enters the chamber 44, the latter may be provided with an elliptical, parabolic or hyperbolic curvature as shown at 48 in FIG. 2*a*.

The inclination of the wall 16 of the housing should preferably be of the order of 50° to 80° with the base of the cone in order to constrict the mist. Since the larger particles emerging through the openings 41 will tend to move outwardly a greater distance than the finer particles, constriction of the mist will have the effect of intercepting the larger particles and thus, provide a more uniformly fine mist. It has been found that particle sizes as small as 0.0056 microns can be produced with this apparatus and while the particles will vary in size, a relatively small portion of the particles exceed 0.1 microns.

As previously pointed out, one of the uses of this invention involves the treatment of lung disorders and for that purpose, the T-tube 15 is utilized. The tube has a tubular portion 50 adapted to engage the tubular portion 13 on the top of the housing 11 and a transverse portion 51. On one end of the transverse portion, there is a tubular outlet 52 of slightly reduced diameter which is adapted to receive a suitable mouthpiece for use by the patient.

The opposing end portion 53 may remain open to the air or may include a cap 54 or other suitable means to restrict or control the flow of air into the T-tube. If desired, a suitable hose can be attached in place of the cap 54 for feeding oxygen or mixtures of oxygen with air as may be desired. The top of the T-tube includes a smaller tubular portion 55 having an opening 56 therein for the purpose of attaching a tube for introducing liquid into the housing 11. By controlling the flow of liquid into the housing, any prescribed quantity of liquid can be nebulized. When feeding liquid through the opening 56, collection on surfaces such as the top cap should be avoided. Accordingly, the top cap 43 is preferably formed with curved upper surfaces on the outwardly extending legs. In this way should one of the legs intercept the liquid drops, they will not collect on the surface. If desired, a second top cap 43' formed in the same manner as the cap 43 may be positioned above the cap 43 and spaced therefrom by a spacer 50'. In such a case, the caps 43 and 43' may be offset by about 45°.

In prior art nebulizers, such as are shown and described in the previously mentioned U.S. Patent Nos. 4,116,387 and 4,456,179, the inverted frusto-conical bottom wall 18 forming the liquid reservoir has a smooth surface and leads in an uninterrupted path directly to passageways 35 for drawing liquid from the reservoir to channels 25. A smooth, uninterrupted path of bottom wall 18 to passageways 35 has been found to render such prior art nebulizers susceptible to "sputtering" prior to complete discharge of liquid from the reservoir. This is because in the prior art devices, droplets of fluid build up along the upper edge of bottom wall 18 and passageways 35 become uncovered prior to complete discharge of liquid when the liquid level drops below the top of the slots 35, admitting air therethrough and causing "sputtering". The present invention overcomes this drawback in the prior art by providing a moat-like, annular liquid-collecting well 18' that is below the bottom wall 18 and has a well rim **18*d* defines the bottom edge of the bottom wall 18 and is above the passageways 35. Because the well rim 18*d* is above the passageways 35, the depth of the well 18' is greater than the height of the passageways 35 and the passageways 35 are covered by the liquid within the well. Slots 35 can have a height within the range of 0.1–1 mm, and a depth within the range of 0.1–1 mm, depending on the viscosity of the fluid to be aerosolized. Preferably, the passageways 35 are in the form of slots. Generally, as the height of the passageways 35 is decreased, the width is increased to pass a given volume of liquid. Although eight passageways 35 are shown in FIG. 8, any suitable number can be used. Liquid that drains from the bottom wall 18 to the well 18' is collected and concentrated between the well outer wall 18*e* and the aspirating structure which is comprised of cylindrical structure 26 and nozzle 19. In the embodiment shown, the moat-like, annular liquid-collecting well 18' is formed between the cylindrical structure 26 and outer well wall 18*e* for collecting liquid to be nebulized. As shown, well 18' is deeper than it is wide, and has a depth that is at least about 1-½ times greater than the height of passageways 35. For example, with a slot height of 1 mm, a well having a depth of 1.5–6 mm is suitable. A suitable well annular width from the edge of the well to the outer wall of cylindrical structure 26 is about 1 mm or less. If desired, the outer wall of the well 18'** can be sloped considerably more off vertical than is shown.

The invention further provides means for directing liquid droplets downwardly towards well 18' in the form of radially extending ridges **18*a* and troughs 18*b* on the upper surface of bottom wall 18. The troughs 18*b* are each defined by two long radially extending ridges 18*f* which are substantially equal in length to the radius of the bottom wall 18. See FIG. 2. Advantageously, ridges are provided of different lengths with more ridges located near the top edge of the bottom wall 18 than near the well, due to convergence of the ridges towards the well. The radial ridges and troughs prevent buildup of droplets on the top edge of the bottom wall 18 by facilitating movement of the droplets directly into well 18'. Additionally, to facilitate movement over the edge of the well, generally vertical grooves 18*c* can be provided along the outer wall of the well 18' that advantageously intersect with ridges 18*a* along bottom wall 18. See FIG. 3**.

In a device according to the invention, as the nebulizer nears complete discharge of liquid, the radially extending ridges and troughs **18*a* and 18*b* direct liquid droplets into the narrow, moat-like liquidcollecting well 18' which concentrates the liquid between the bottom wall 18 and nozzle, and keeps the slots 35** covered with liquid for substantially longer than the prior art devices and until substantially complete discharge of liquid from the reservoir. The present invention thus provides more uniform delivery of nebulized liquid than prior art devices by avoiding "sputtering" of the liquid prior to substantially complete discharge of the liquid from the reservoir. If desired, certain aspects of the features of the invention can be varied to modify particle size or alter the rate of aerosolization of the liquid and the like, while avoiding sputtering in the device.

While only certain embodiments of the invention have been illustrated and described, it is understood that alterations, changes and modifications may be made without departing from the true scope and spirit thereof.

What is claimed is:

1. A nebulizer comprising a housing having a mist outlet, an aspirating structure including a nozzle having a base portion at one end thereof within the housing and a nozzle outlet for the discharge of gas under pressure within the housing at an end of the nozzle opposite the base portion, the nebulizer further comprising a sidewall and an inverted frusto-conical bottom wall disposed about the base portion of the nozzle away from the nozzle outlet, the bottom wall forming a liquid reservoir that drains towards the base portion of the aspirating structure, the nebulizer further including a well below said bottom wall for collecting and concentrating liquid between the outer wall of the well and the aspirating structure to avoid sputtering of liquid prior to substantially complete discharge of liquid from the nebulizer, said well having a well rim that defines the bottom edge of said bottom wall, the aspirating structure further including at least one passageway peripherally located with respect to said nozzle, said passageway being located below said well rim, said passageway communicating with the well for the aspiration of liquid from the well in response to gas discharged from said nozzle to form a mist.

2. The nebulizer of claim 1 wherein the nozzle is tubular.

3. The nebulizer of claim 1 wherein said well is an annular well disposed about the aspirating structure.

4. The nebulizer of claim 1 wherein the nozzle is tubular and said well is an annular well disposed about the aspirating structure.

5. The nebulizer of claim 1 including a plurality of said passageways, said passageways having separate openings into said well, said openings being in the form of slots.

6. The nebulizer of claim 5 wherein said slots extend upwardly from the bottom of said well, and said well has a depth which is at least about 1-½ times greater than the height of said slots.

7. The nebulizer of claim 6 wherein the slots have a height of about 0.1–1 mm and a width of about 0.1–1 mm.

8. The nebulizer of claim 7 wherein the well has an annular width of about 1 mm or less.

9. The nebulizer of claim 1 further including radially extending troughs which are defined by radially extending ridges on the upper surface of the bottom wall, between the well and the sidewall.

10. The nebulizer of claim 9 further including substantially vertical grooves along an outer wall of said well.

11. The nebulizer of claim 1 wherein the an inner portion of the sidewall includes a plurality of ridges.

12. A nebulizer comprising a housing having a mist outlet, an aspirating structure including a nozzle having a base portion at one end thereof within the housing and a nozzle outlet for the discharge of gas under pressure within the housing at an end of the nozzle opposite the base portion, the nebulizer further comprising an inverted frusto-conical bottom wall disposed about the base portion of the nozzle away from the nozzle outlet, the bottom wall forming a liquid reservoir that drains towards the base portion of the nozzle, the aspirating structure further including at least one passageway peripherally located with respect to said nozzle, said passageway communicating with the reservoir for the aspiration of liquid from the reservoir in response to gas discharged from said nozzle to form a mist, the nebulizer further including a well interposed between the bottom wall and the aspirating structure for collecting and concentrating liquid between said bottom wall and said aspirating structure and radially extending ridges on the upper surface of said bottom wall for directing liquid droplets into said well to avoid sputtering of liquid prior to substantially complete discharge of liquid from the nebulizer.

* * * * *